(12) United States Patent
Nagao et al.

(10) Patent No.: US 8,377,029 B2
(45) Date of Patent: Feb. 19, 2013

(54) DRUG SOLUTION FILLING PLASTIC AMPOULE AND PROCESS FOR PRODUCING THE SAME

(75) Inventors: Katsuyoshi Nagao, Tokushima (JP); Hideshi Okamoto, Tokushima (JP); Masamitsu Izumi, Naruto (JP); Keiichi Kawakami, Tokushima (JP); Fujio Inoue, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 9 days.

(21) Appl. No.: 10/554,094

(22) PCT Filed: Apr. 19, 2004

(86) PCT No.: PCT/JP2004/005547
§ 371 (c)(1),
(2), (4) Date: Oct. 21, 2005

(87) PCT Pub. No.: WO2004/093775
PCT Pub. Date: Nov. 4, 2004

(65) Prior Publication Data
US 2006/0229583 A1    Oct. 12, 2006

(30) Foreign Application Priority Data

Apr. 23, 2003  (JP) .................................. 2003-118901
Oct. 24, 2003  (JP) .................................. 2003-364971

(51) Int. Cl.
*A61B 19/00*   (2006.01)
*A61M 5/28*    (2006.01)
*A61M 5/00*    (2006.01)
*B65D 53/00*   (2006.01)
*B65D 53/06*   (2006.01)
*B65D 1/09*    (2006.01)

(52) U.S. Cl. ........ 604/403; 604/200; 604/212; 604/217; 604/244; 604/415; 220/255; 220/255.1; 215/47; 215/48; 215/49

(58) Field of Classification Search .................. 604/403, 604/200, 212, 217, 244
See application file for complete search history.

(56) References Cited

U.S. PATENT DOCUMENTS 3,892,058 A * 7/1975 Komatsu et al. ................. 53/425
4,502,616 A * 3/1985 Meierhoefer .................. 222/215
(Continued)

FOREIGN PATENT DOCUMENTS

EP    0 326 391 A2    8/1989
GB    991495         5/1965
(Continued)

OTHER PUBLICATIONS

Online encyclopedia, "Polyol." Accessed Aug. 3, 2007 http://en.wikipedia.org/wiki/Polyol.*

(Continued)

*Primary Examiner* — Leslie Deak
*Assistant Examiner* — Adam Marcetich
(74) *Attorney, Agent, or Firm* — Finnegan, Henderson, Farabow, Garrett & Dunner, L.L.P.

(57) ABSTRACT

A drug solution filling plastic ampoule having gas, steam and light ray barrier properties, a drug permeation preventing capability and an absorption/adsorption preventing capability, and a production method for the plastic ampoule. The drug solution filling plastic ampoule includes a container body, a fusion-bonded portion which seals a mouth of the container body, and a wrench-off holder tab connected to the fusion-bonded portion. The ampoule is formed from a parison including two or more layers, at least one of which is a functional layer having at least one characteristic property selected from the group consisting of a gas permeation preventing capability, a steam permeation preventing capability, a light ray permeation preventing capability, a drug permeation preventing capability and a drug absorption/adsorption preventing capability.

6 Claims, 2 Drawing Sheets

U.S. PATENT DOCUMENTS

| | | | | |
|---|---|---|---|---|
| 4,512,475 | A * | 4/1985 | Federighi | 206/484 |
| 4,529,095 | A | 7/1985 | Hansen | |
| 4,537,305 | A * | 8/1985 | Takanashi | 206/438 |
| D289,200 | S * | 4/1987 | Newell | D24/117 |
| 5,561,208 | A | 10/1996 | Takahashi et al. | |
| 5,723,189 | A | 3/1998 | Sudo | |
| 5,968,616 | A * | 10/1999 | Kakemura et al. | 428/34.2 |
| 6,042,906 | A * | 3/2000 | Itoh et al. | 428/35.2 |
| 6,068,936 | A * | 5/2000 | Peiffer et al. | 428/500 |
| 6,165,573 | A * | 12/2000 | Hirose et al. | 428/36.6 |
| 6,254,376 | B1 * | 7/2001 | Louviere | 425/547 |
| 6,255,396 | B1 * | 7/2001 | Ding et al. | 525/191 |
| 6,479,138 | B1 * | 11/2002 | Childress | 428/213 |
| 6,572,603 | B1 * | 6/2003 | Tani et al. | 604/403 |
| 6,713,165 | B1 * | 3/2004 | Karsten | 428/213 |
| 6,872,462 | B2 * | 3/2005 | Roberts et al. | 428/516 |
| 7,179,521 | B2 * | 2/2007 | Arthurs et al. | 428/213 |
| 2002/0098310 | A1 * | 7/2002 | Kikuchi et al. | 428/36.91 |
| 2002/0132077 | A1 * | 9/2002 | Ling et al. | 428/36.91 |
| 2002/0160135 | A1 * | 10/2002 | Christopherson et al. | 428/35.7 |
| 2002/0187326 | A1 * | 12/2002 | Kong | 428/220 |
| 2002/0192412 | A1 * | 12/2002 | Satani et al. | 428/35.7 |
| 2002/0197478 | A1 * | 12/2002 | Muggli et al. | 428/411.1 |
| 2003/0140923 | A1 * | 7/2003 | Taylor et al. | 128/203.12 |
| 2003/0180560 | A1 * | 9/2003 | Peiffer et al. | 428/480 |
| 2004/0067382 | A1 * | 4/2004 | Niepelt | 428/515 |
| 2004/0142195 | A1 * | 7/2004 | Roberts et al. | 428/515 |

FOREIGN PATENT DOCUMENTS

| | | |
|---|---|---|
| JP | 33-8078 | 9/1933 |
| JP | 36-5985 | 5/1936 |
| JP | 60-24844 | 2/1985 |
| JP | 5-277154 | 10/1993 |
| JP | 5-293159 | 11/1993 |
| JP | 07-171858 | 7/1995 |
| JP | 8-34422 | 2/1996 |
| JP | 08-267679 | 10/1996 |
| JP | 9-70876 | 3/1997 |
| JP | 09-239909 | 9/1997 |
| JP | 10-59343 | 3/1998 |
| JP | 2914826 | 4/1999 |
| JP | 2000-072124 | 3/2000 |
| JP | 2000-238847 | 9/2000 |
| JP | 2000-262591 | 9/2000 |
| JP | 2000-279486 | 10/2000 |
| JP | 2000-309372 | 11/2000 |
| JP | 2001-26718 | 1/2001 |
| JP | 2001-070399 | 3/2001 |
| JP | 2002-068963 | 3/2002 |
| JP | 2002-291841 | 8/2002 |
| JP | 2002-301796 | 10/2002 |
| JP | 2002-337290 | 11/2002 |
| JP | 2003-072003 | 3/2003 |
| JP | 2003-118718 | 4/2003 |

OTHER PUBLICATIONS

Online dictionary, "parison." Accessed Aug. 4, 2007 http://dictionary.reference.com/search?q=parison&r=66.*

Mutual's Home Page, "Packaging Equipment—Container Forming and Aseptic Filling System", http://www.mutual.co.jp (Mar. 19, 2003).

Nissin Pharmaceutical's Home Page; "Polyethylene Bottle", http://www.vg-nissin.co.ip/BFS.htm (Mar. 19, 2003).

Rommelag's Home Page; "Welcome to Rommelag" and "BTS Process—The Bottlepack Process", http://www.rommelag.com (Mar. 19, 2003).

Supplementary European Search Report dated Jun. 8, 2011 issued in EP application No. 04728250.4.

Japanese Office Action dated Nov. 15, 2012 issued in corresponding Japanese Patent Appln. 2012-000627; pp. 1-3.

* cited by examiner

DRUG SOLUTION FILLING PLASTIC AMPOULE AND PROCESS FOR PRODUCING THE SAME

TECHNICAL FIELD

The present invention relates to a plastic ampoule filled with a drug solution. More specifically, the invention relates to a drug solution filling plastic ampoule which is capable of preventing steam, gases other than steam, light rays or a pharmaceutical preparation (a drug, a drug solution and a solvent for the drug solution) from intruding into or leaking out of the ampoule, or preventing the drug, the drug solution or the solvent contained in the ampoule from being absorbed in or adsorbed on an interior surface of the ampoule, and to a production method for the plastic ampoule.

BACKGROUND ART

Conventional ampoules for containing a drug solution are mostly composed of glass. However, if a drug solution contained in such a glass ampoule has a higher pH, alkali flakes are liable to leach out of the ampoule. When the ampoule is opened, the ampoule is liable to cause injuries to one's fingers. Further, there are risks of fracture of the ampoule and contamination of the drug solution with shards of the ampoule produced when the ampoule is opened. The United States Food and Drug Administration (FDA) gives an advice against a risk that aluminum contained in the glass of the ampoule is liable to leach into the drug solution. In recent years, the glass ampoules have been replaced with plastic ampoules which are free from these risks.

Polyolefins such as polyethylene (PE) and polypropylene (PP) which are flexible and highly safe are typically used as a plastic material for the ampoule. The PE and the PP are highly stable against acidic drugs and alkaline drugs, but highly absorbent of and highly permeable to oxygen, air and carbon dioxide gas, etc. Therefore, the PE and the PP are not suitable as a material for an ampoule for containing an easily oxidizable drug or drug solution. Particularly, where the ampoule has a smaller volume, the content of the ampoule is reduced due to moisture permeation, thereby resulting in remarkable increase of the concentration of the drug in the drug solution.

Therefore, it is contemplated to use multilayer materials (laminate materials) imparted with gas and steam permeation preventing capabilities (barrier properties) as materials for film-formed products such as infusion bags and blow-molded products such as infusion bottles.

Plastic laminate materials are widely used for production of films and sheets. However, it is not appropriate to use such a film or a sheet for the production of the ampoule, so that the blow-molding method is inevitably employed for the production of the ampoule.

Ampoules produced by the blow-molding are disclosed in Japanese Patent Publication No. 2914826 and Japanese Unexamined Patent Publication No. SHO60 (1985)-24844. An ampoule (a sanitary product container) disclosed in the former publication is blow-molded from a polycycloolefin. An ampoule (a container for containing an injection drug) disclosed in the latter publication includes an air barrier layer of a material obtained by saponification of an ethylene-vinyl acetate copolymer (EVA) as an intermediate layer.

However, these publications merely teach that the ampoules are produced by the blow-molding. According to these publications, the sealing of each of the ampoules is achieved by heat-sealing an opening of the ampoule without formation of a seam after injecting a drug solution or charging a drug into the ampoule. In this case, the multilayer structure is liable to be broken by heat applied for the heat-sealing. As a result, the function and effect (the gas permeation preventing capability and the like) provided by employing the multilayer structure including the polycycloolefin or EVA layer are deteriorated.

Another production method for a drug solution filling plastic ampoule is a so-called blow-fill-seal process (see Japanese Examined Patent Publications No. SHO33 (1958)-8078 and No. SHO36 (1961)-5985, rommelag's Home Page "Welcome to Rommelag®" and "BFS Process—The Bottelpack® Process" retrieved from URL http://www.rommelag.com/ on Internet on Mar. 19, 2003).

The blow-fill-seal process includes the steps of forming an ampoule body by holding a tubular molten plastic parison by a main mold, filling a drug solution in the ampoule body, forming a head of an ampoule by a head mold, and sealing the ampoule, which are sequentially performed. Since the ampoule forming step, the drug solution filling step and the ampoule sealing step are sequentially performed, the blow-fill-seal process significantly differs from a simple blow-molding process, and the filling of the drug solution can be achieved more aseptically. In addition, the blow-fill-seal process is advantageous in that mass production can be realized.

However, a known ampoule produced by the blow-fill-seal process is a single layer ampoule composed of a polyolefin such as PE or PP. Therefore, it has not been contemplated to produce the ampoule of the laminate structure by the blow-fill-seal method and to impart one of the layers of the laminate structure with gas, steam, light ray and drug permeation preventing capabilities (barrier properties) and a drug absorption/adsorption preventing capability (see Japanese Examined Patent Publications No. SHO33 (1958)-8078 and No. SHO36 (1961)-5985, the aforementioned rommelag's Home Page, Mutual's Home Page "Packaging equipment—Container forming and aseptic filling system" retrieved from URL http://www.mutual.co.jp on Internet on Mar. 19, 2003, and Nisshin Pharmaceutical's Home Page "Polyethylene bottle" retrieved from URL http://www.yg-nissin.co.jp/BFS.htm on Internet on Mar. 19, 2003).

Exemplary methods for imparting the gas, steam, light ray and drug permeation preventing capabilities (barrier properties) and the drug absorption/adsorption preventing capabilities are to store the ampoule in a bag having a gas permeation resistance and to cover the surface of the ampoule with a material having the light ray permeation preventing capability (light barrier property) or with an exterior package. However, these methods additionally require the storage bag and materials for the surface coverage, thereby complicating the production process and increasing the production costs.

DISCLOSURE OF THE INVENTION

It is therefore an object of the present invention to provide a drug solution filling plastic ampoule which is capable of preventing steam, gases other than steam, light rays or a drug from intruding into or leaking out of the ampoule, or preventing a drug, a drug solution or a solvent contained in the ampoule from being absorbed in or adsorbed on an interior surface of the ampoule, and a production method for the plastic ampoule.

To solve the aforementioned problems, a drug solution filling plastic ampoule according to the present invention comprises a flexible container body, a fusion-bonded portion which seals a mouth of the container body, and a holder tab connected to the fusion-bonded portion for wrenching off the fusion-bonded portion. The container body, the fusion-bonded portion and the holder tab are integrally molded from a tubular parison including two or more layers. The container body is molded by holding the parison between split mold pieces and, after a drug solution is filled in the container body, the mouth is sealed. At least one of the layers of the parison is a functional layer having at least one characteristic property selected from the group consisting of a gas permeation preventing capability, a steam permeation preventing capability, a light ray permeation preventing capability, a drug permeation preventing capability and a drug absorption/adsorption preventing capability.

The blow-fill-seal process is employed for the production of the drug solution filling plastic ampoule, so that the filling of the drug solution and the sealing of the ampoule can be achieved aseptically. In addition, the drug solution filling plastic ampoule according to the present invention is free from breakage of the layer structure of the fusion-bonded portion of the mouth, unlike the ampoule produced by filling a drug in an empty blow-molded ampoule and fusion-bonding an opening of the ampoule without formation of a seam (disclosed in Japanese Patent Publication No. 2914826 and Japanese Unexamined Patent Publication No. SHO60 (1985)-24844). Therefore, the drug solution filling plastic ampoule sufficiently exhibits desired characteristic properties (the gas barrier property and the like) after the molding of the ampoule.

Characteristic properties required for the functional layer in the present invention are the gas permeation preventing capability (gas barrier property) the steam permeation preventing capability (steam barrier property), the light ray permeation preventing capability (light ray barrier property), the drug permeation preventing capability (drug barrier property) and the drug absorption/adsorption preventing capability. These characteristic properties depend on a plastic material for the functional layer of the parison and ingredients of the plastic material as will be described later.

A drug solution filling plastic ampoule adapted to be opened by wrenching off a holder tab is disclosed in Japanese Unexamined Patent Publication No. 2001-70399, which states (in paragraphs [0007] and [0012]) that the ampoule is produced by the blow-fill-seal process and that the ampoule is formed as having a layer structure or is imparted with a light blocking property as required. However, the patent publication neither expressly nor implicitly teaches that the parison per se has a layer structure and the parison includes a layer composed of a functional material having any of the aforesaid properties to impart the ampoule with the desired barrier property.

The parison to be used for the molding of the drug solution filling plastic ampoule according to the present invention preferably has an innermost layer composed of a resin comprising a polyolefin or a polycycloolefin.

By using the resin comprising the polyolefin or the polycycloolefin as a material for the innermost layer of the parison, the drug solution filling plastic ampoule also has an innermost layer composed of the resin comprising the polyolefin or the polycycloolefin. Since the polyolefin and the polycycloolefin are stable and safe, the drug solution filling plastic ampoule having the innermost layer composed of the polyolefin or the polycycloolefin is safely employed as a medical container.

The parison to be used for the molding of the drug solution filling plastic ampoule according to the present invention includes at least one layer provided as other than the innermost layer and composed of a material containing at least one additive selected from the group consisting of a colorant, a UV absorbing agent and an oxygen absorbing agent, and a layer provided inward of the additive-containing layer and having a drug permeation preventing capability.

Where the at least one layer provided as other than the innermost layer contains the colorant and/or the UV absorbing agent, the drug solution filling plastic ampoule is imparted with the light ray permeation preventing capability (light ray barrier property, more specifically, a light/UV barrier property). Where the at least one layer provided as other than the innermost layer contains the oxygen absorbing agent, the drug solution filling plastic ampoule is imparted with the oxygen permeation preventing capability (oxygen barrier property).

If the layer containing the colorant, the UV absorbing agent or the oxygen absorbing agent is in direct contact with the drug solution, the colorant or the like is liable to leach out of the layer. In the drug solution filling plastic ampoule, however, the layer having the drug permeation preventing capability is disposed inward of the layer containing the colorant or the like. This prevents the colorant or the like from leaching out of the ampoule into the drug solution contained in the ampoule.

Examples of the layer having the drug permeation preventing capability and disposed inward of the layer containing the colorant or the like include a polyol layer, a polyester layer and a polycycloolefin layer.

The functional layer of the parison for the molding of the drug solution filling plastic ampoule according to the present invention preferably includes:

(i) a polyamide layer;
(ii) a polyol layer;
(iii) a polyester layer; or
(iv) a polycycloolefin layer.

Where the functional layer includes the polyamide layer (i), the drug solution filling plastic ampoule is imparted with the gas permeation preventing capability and the steam permeation preventing capability. Therefore, this ampoule is employed, for example, as a container for containing a drug solution which is liable to be oxidized and hence cannot be stored in the presence of oxygen, or a container for containing a drug solution whose efficacy or the like is liable to significantly change due to a change in moisture content.

Where the functional layer includes the polyol layer (ii), the drug solution filling plastic ampoule is imparted with the gas permeation preventing capability, the steam permeation preventing capability, the drug permeation preventing capability and the drug absorption/adsorption preventing capability. Therefore, this ampoule is employed, for example, as a container for containing a drug solution which cannot be stored in the presence of oxygen, or a container for containing a drug solution whose efficacy or the like is liable to significantly change due to a change in moisture content.

Where the ampoule includes the layer which contains any of the additives such as the colorant, the UV absorbing agent and the oxygen absorbing agent, for example, provision of the polyol layer inward of the additive-containing layer prevents the additives from leaching into the drug solution contained in the ampoule.

Where the functional layer includes the polyester layer (iii), the drug solution filling plastic ampoule is imparted with the gas permeation preventing capability, the steam permeation preventing capability, the drug permeation preventing capability and the drug absorption/adsorption preventing capability. Therefore, this ampoule is employed, for example, as a container for containing a drug solution which cannot be stored in the presence of oxygen, or a container for containing a drug solution whose efficacy or the like is liable to significantly change due to a change in moisture content. The use of the polyester layer as the innermost layer of the ampoule prevents the drug from being absorbed in or adsorbed on the innermost layer of the ampoule.

The polycycloolefin is advantageous in that it has the drug absorption/adsorption preventing capability, the drug permeation preventing capability (drug barrier property) and the steam permeation preventing capability and is excellent in transparency. Therefore, an attempt is made to use the polycycloolefin as a material for medical containers (Japanese Unexamined Patent Publication No. HEI5 (1993)-277154). Where the functional layer includes the polycycloolefin layer (iv), the drug solution filling plastic ampoule is imparted with the drug permeation preventing capability (drug barrier property), the drug absorption/adsorption preventing capability and the steam permeation preventing capability.

Where the ampoule includes the layer containing any of the additives such as the colorant, the UV absorbing agent and the oxygen absorbing agent, for example, provision of the polycycloolefin layer inward of the additive-containing layer prevents the additives from leaching into the drug solution contained in the ampoule.

The use of the polycycloolefin layer as the innermost layer of the ampoule prevents the drug from being absorbed in or adsorbed on the innermost layer of the ampoule. In this case, the polycycloolefin to be used for formation of the innermost layer preferably has a glass transition temperature (Tg) of not higher than 110° C. The use of the polycycloolefin having a glass transition temperature within the aforesaid range as the material for the innermost layer prevents the drug solution from leaking from a joint of the mold (a joint between a main mold and a head mold) used in the blow-fill-seal process after the filling of the content liquid and the sealing of the ampoule. Particularly, the glass transition temperature of the polycycloolefin is preferably 60 to 105° C., more preferably 60 to 80° C., within the aforesaid range.

Japanese Unexamined Patent Publication No. HEI5 (1993)-293159 discloses an ampoule molded from the polycycloolefin. However, this publication mentions nothing about the production of the ampoule by the blow-fill-seal process, and implies nothing about the problem of the aforesaid liquid leakage and measures against this problem.

On the other hand, a polycycloolefin having a glass transition temperature of higher than 110° C. is generally poor in flexural stress resistance and brittle. Therefore, where the drug solution filling plastic ampoule is formed of a laminate including an innermost layer of the polycycloolefin having a glass transition temperature of not higher than 110° C. and a layer of the polycycloolefin having a glass transition temperature of higher than 110° C., it is possible to prevent the liquid leakage after the filling of the content liquid and the sealing of the ampoule while ensuring easy opening of the ampoule by bending or wrenching off the fusion-bonded portion (thin wall portion) of the ampoule.

Products molded from a non-cyclic olefin polymer are generally more flexible and more excellent in shock resistance than those molded from the polycycloolefin. Therefore, where the laminate used as the material for the plastic ampoule includes not only the polycycloolefin layer but also a non-cyclic polyolefin layer, the plastic ampoule has an improved shock resistance as a whole.

The drug solution filling plastic ampoule according to the present invention may be an ampoule sequence including a plurality of ampoules connected to one another via severable thin wall portions. The ampoule sequence facilitates management of the plurality of ampoules which contain the same type of drug solution.

Where the functional layer of the drug solution filling plastic ampoule according to the present invention has the steam permeation preventing capability or the drug absorption/adsorption preventing capability, the drug solution filling plastic ampoule is usable as an ampoule having a volume of 0.5 to 20 mL. That is, the plastic ampoule including the polyamide layer (i), the polyol layer (ii), the polyester layer (iii) or the polycycloolefin layer (iv) as the functional layer is advantageously employed as a smaller volume ampoule having a volume of 0.5 to 20 mL. The ampoule having a volume of 0.5 to 20 mL contains a smaller absolute amount of content liquid, so that the properties of the content liquid is liable to significantly change when a solvent of the content liquid contained in the ampoule evaporates or the drug is absorbed in or adsorbed on the ampoule. However, this problem is prevented by the provision of the polyamide layer, the polyol layer, the polyester layer or the polycycloolefin layer excellent in the steam permeation preventing capability and the drug absorption/adsorption preventing capability.

A production method for the drug solution filling plastic ampoule according to the present invention comprises the steps of: molding a container body by holding a tubular parison between lower split mold pieces and forming a void in the parison, the parison having at least two layers, at least one of which is a functional layer having at least one characteristic property selected from the group consisting of a gas permeation preventing capability, a steam permeation preventing capability, a light ray permeation preventing capability, a drug permeation preventing capability and a drug absorption/adsorption preventing capability; filling a drug solution in the container body; and holding a mouth of the container body between upper split mold pieces to form a fusion-bonded portion which seals the mouth of the container body and a holder tab which is connected to the fusion-bonded portion to be used for wrenching off the fusion-bonded portion.

In the production process, the filling of the drug solution in the drug solution filling plastic ampoule and the sealing of the ampoule can be achieved aseptically. In addition, the formation of the fusion-bonded portion can be achieved without breaking the multilayer plastic laminate structure when the mouth of the ampoule is fusion-bonded and sealed after the filling of the drug solution.

Therefore, the aforesaid inventive production method is very advantageous for production of a drug solution filling plastic ampoule which is capable of preventing a gas, steam, light rays and a drug from intruding into or leaking out of the ampoule or preventing a drug, a drug solution or a solvent contained in the ampoule from being absorbed in or adsorbed on an interior surface of the ampoule.

In the production method for the drug solution filling plastic ampoule according to the present invention, the parison preferably includes:
(a) an innermost layer composed of a resin comprising a polyolefin or a polycycloolefin; or
(b) at least one layer provided as other than the innermost layer and containing at least one additive selected from the group consisting of a colorant, a UV absorbing agent and an oxygen absorbing agent, and a layer provided inward of the additive-containing layer and having a drug permeation preventing capability.

In the case (a), the drug solution filling plastic ampoule produced by the aforesaid method is more safely used as a medical container.

Where the innermost layer is composed of a resin comprising the polycycloolefin in the case (a), the polycycloolefin preferably has a glass transition temperature of not higher than 110° C., more preferably a glass transition temperature of 60 to 105° C., for the aforementioned reasons.

In the case (a), the parison preferably includes an innermost layer composed of a polycycloolefin having a glass transition temperature of not higher than 110° C., and a layer composed of a polycycloolefin having a glass transition temperature of higher than 110° C. for the aforementioned reasons.

In the case (b), the drug solution filling plastic ampoule produced by the aforesaid method is imparted with a light ray permeation preventing capability (light/UV barrier property).

BEST MODE FOR IMPLEMENTING THE INVENTION

A drug solution filling plastic ampoule and a production method therefor according to the present invention will hereinafter be described in detail with reference to the drawings.
Drug Solution Filling Plastic Ampoule FIGS. 1 and 2 are diagrams illustrating embodiments of the drug solution filling plastic ampoule according to the present invention.

Figure 1:
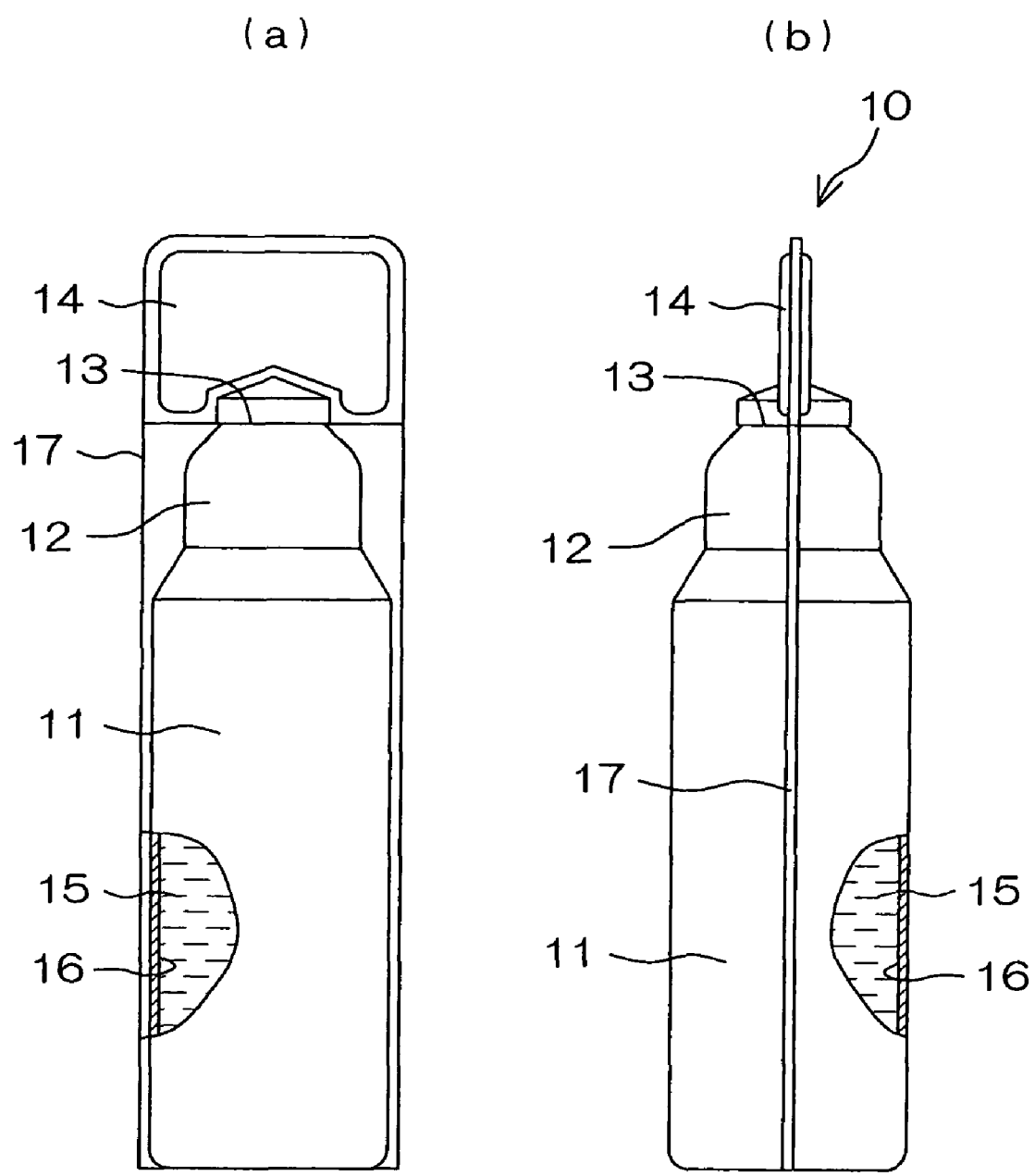
FIGS. 1(a) and 1(b) are a partly cutaway front view and a partly cutaway right side view, respectively, illustrating one embodiment of a drug solution filling plastic ampoule according to the present invention.

A drug solution filling plastic ampoule 10 shown in FIG. 1 includes a flexible container body 11, a fusion-boned portion 13 which seals a mouth 12 of the container body, and a holder tab 14 connected to the fusion-bonded portion 13.

Figure 2:
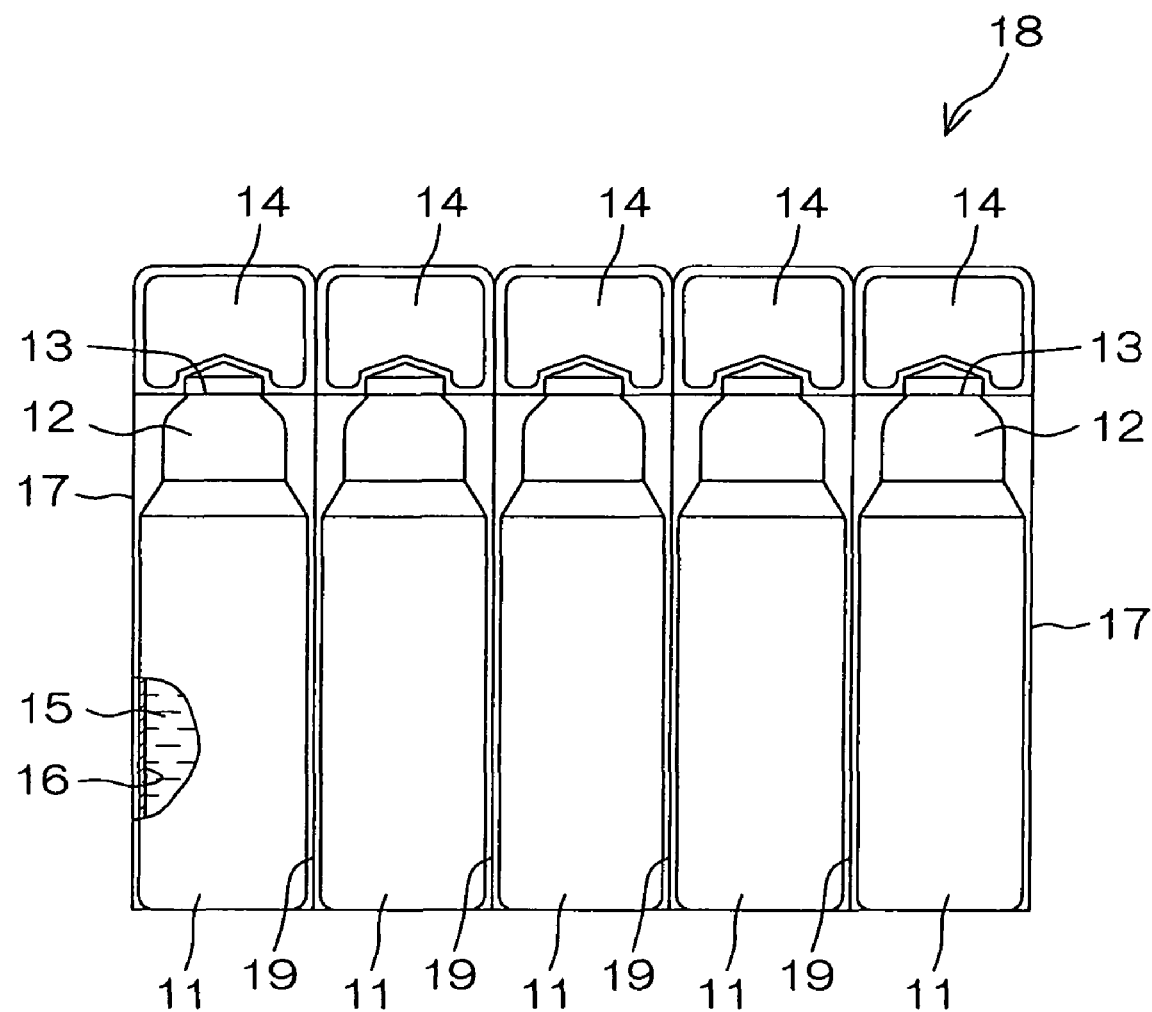
FIG. 2 is a partly cutaway front view illustrating another embodiment of the drug solution filling plastic ampoule according to the present invention.

Like the ampoule 10 shown in FIG. 1, drug solution filling plastic ampoules 18 shown in FIG. 2 each include a flexible container body 11, a fusion-boned portion 13 which seals a mouth 12 of the container body, and a holder tab 14 connected to the fusion-bonded portion 13. Side edges 17 of the ampoules 18 are connected to one another via severable connection portions 19.

The holder tab 14 of the drug solution filling plastic ampoule is bent or wrenched so as to be separated from the fusion-bonded portion 13. By wrenching off the holder tab 14 and separating the holder tab 14 from the fusion-bonded portion 13 and the container body 11, the mouth 12 of the container body 11 is opened, so that a drug solution 15 filled and sealed in the container body 11 can be dispensed or discharged.

Where the ampoules 10, 18 are each composed of a laminate including a polycycloolefin having a glass transition temperature of higher than 110° C., the separation of the fusion-bonded portion 13 is facilitated for the aforementioned reasons.

A plastic material 16 for the drug solution filling plastic ampoules includes at least one functional layer which has at least one characteristic property selected from the group consisting of a gas permeation preventing capability, a steam permeation preventing capability, a light ray permeation preventing capability, a drug permeation preventing capability and a drug absorption/adsorption preventing capability.

The side edges 17 of the drug solution filling plastic ampoules are formed by holding a parison between mold pieces in molding the ampoules by the blow-fill-seal process. The molding of the drug solution filling plastic ampoules 18 is achieved, for example, with the use of a multi-head unit including heads and dies corresponding in number to the ampoules to be connected to one another.
Ampoule Material As described above, the functional layer of the inventive drug solution filling plastic ampoule has at least one characteristic property selected from the group consisting of the gas permeation preventing capability, the steam permeation preventing capability, the light ray permeation preventing capability, the drug permeation preventing capability and the drug absorption/adsorption preventing capability. These properties are related to the types of plastic materials for the functional layer as described above.

Exemplary polyamides usable in the present invention include 6-nylon, 6,6-nylon, 6,12-nylon, 12-nylon and xylylenediamine polyamide, but are not limited to these polyamides.

Exemplary polyesters usable in the present invention include polyethylene terephthalate (PET), polyethylene naphthalate, polybutylene terephthalate (PBT), but are not limited to these polyesters.

Exemplary polyols usable in the present invention include polyvinyl alcohol (PVOH) and ethylene-vinyl alcohol copolymers (EVOH), but are not limited to these polyols.

Exemplary polycycloolefins usable in the present invention include copolymers of ethylene and dicyclopentadienes, copolymers of ethylene and norbornene compounds, polymers obtained by ring-opening polymerization of cyclopentadiene derivatives and copolymers obtained by ring-opening polymerization of plural types of cyclopentadiene derivatives, and hydrogenated compounds of these polymers and copolymers, but are not limited to these polycycloolefins.

Among the exemplary polycycloolefins described above, hydrogenated compounds of the copolymers of ethylene and norbornene compounds and hydrogenated compounds of (co)polymers obtained by ring-opening polymerization of at least one type of cyclopentadiene derivatives are particularly preferred for use in the present invention. The use of any of these polycycloolefins further improves the strength and the moisture permeation preventing capability of the ampoules, and imparts the ampoules with the gas permeation preventing capability.

The polycycloolefin may be, for example, a polymer having a repeating unit represented by the following general formula (1) and a repeating unit represented by the following general formula (1'), or a polymer having a repeating unit represented by the following general formula (2):

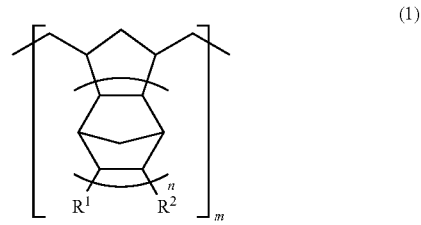

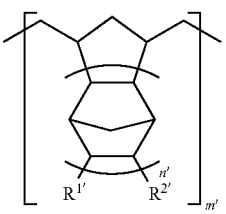

(1')

wherein $R^1$, $R^{1'}$, $R^2$ and $R^{2'}$, which may be the same or different, are each hydrogen, a hydrocarbon residue or a polar group such as a halogen, an ester group, a nitrile group or a pyridyl group; $R^1$, $R^{1'}$, $R^2$ and $R^{2'}$ may be combined to form a ring; m and m' are each an integer not smaller than 1; and n and n' are each 0 or an integer not smaller than 1,

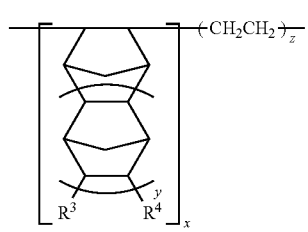

(2)

wherein $R^3$ and $R^4$, which may be the same or different, are each hydrogen, a hydrocarbon residue or a polar group such as a halogen, an ester group, a nitrile group or a pyridyl group; $R^3$ and $R^4$ may be combined to form a ring; x and z are each an integer not smaller than 1; and y is 0 or an integer not smaller than 1.

The polymer having the repeating units represented by the general formulae (1) and (1') is obtained by polymerizing one type or two or more types of monomers by a known ring-opening polymerization method and optionally hydrogenating the resulting ring-opened polymer by an ordinary method. Specific examples of the polymer include ZEONOR (registered trademark) available from Nippon Zeon Co., Ltd. and ARTON (registered trademark) available from Japan Synthetic Rubber Co., Ltd.

The polymer having the structural unit represented by the general formula (2) is obtained by copolymerizing one type or two or more types of norbornene monomers and an ethylene monomer by a known addition copolymerization method and optionally hydrogenating the resulting copolymer by an ordinary method. Specific examples of the polymer include APEL (registered trademark) available from Mitsui Chemicals Inc.) and TOPAS (registered trademark) available from Ticona GmBH.

The hydrogenated polymer having the repeating units represented by the general formulae (1), (1') and the hydrogenated polymer having the repeating unit represented by the general formula (2) are saturated polymers and, therefore, are excellent in gas barrier property, moisture barrier property, heat resistance, transparency and stability.

From the viewpoint of the moldability and the dynamic properties of the ampoules, it is preferred that the polycycloolefin to be used in the present invention has a melt flow rate (MFR) of 4 to 30 g/10 min (at 190° C.).

The molecular weight of the polycycloolefin to be used in the present invention is not particularly limited, but preferably has a number average molecular weight <Mn> of 10,000 to 100,000, more preferably 20,000 to 50,000. The molecular weight is measured, for example, by a gel permeation chromatography (GPC) analysis using cyclohexane as a solvent.

In the present invention, other examples of the resin usable for the formation of the functional layer include a modified polyolefin, polyvinylidene chloride (for the gas permeation preventing capability and the steam permeation preventing capability), and polyacrylonitrile (for the gas permeation preventing capability, the steam permeation preventing capability, the drug permeation preventing capability and the drug absorption/adsorption preventing capability).

Examples of the modified polyolefin include polyolefins modified by adding a functional group such as a carboxyl group to polyolefins (nonpolar polymers) such as polyethylene and polypropylene (e.g., a polyolefin modified by graft-polymerizing an unsaturated carboxylic acid such as maleic acid). Specific examples of the modified polyolefin include adhesive polyolefins available from Mitsui Chemicals Inc. under the trade names of ADMER® LB540, ADMER® NF510 and ADMER® UF300 and highly adhesive resins available from Mitsubishi Chemical Corporation under the trade names of MODIC®-AP P512V and MODIC®-AP L103. The modified polyolefin is properly selected from these polyolefins depending on the type of the resin for the layer to be bonded.

For the formation of the layer having the light ray permeation preventing capability (light ray barrier property), any of the following pigments and UV absorbing agents may be blended in the plastic material. Examples of the pigment to be used for preparation of a material having the light ray barrier property include inorganic pigments such as titanium oxide, zinc oxide, carbon black, red oxide and silicon dioxide, and organic pigments such as phthalocyanine pigments, azo pigments and quinacridone pigments, but are not limited to these pigments.

Examples of the UV absorbing agent to be used for preparation of a material having the light ray barrier property include: salicylate-based UV absorbing agents such as phenyl salicylate and p-octyl phenyl salicylate; benzophenone-based UV absorbing agents such as 2,4-hydroxybenzophenone and bis(2-methoxy-4-hydroxy-5-benzoylphenyl)methane; cyanoacrylate-based UV absorbing agents such as 2-ethylhexyl-2-cyano-3,3-diphenyl acrylate and ethyl-2-cyano-3,3-diphenyl acrylate; and benzotriazole-based UV absorbing agents such as 2-(5-methyl-2-hydroxyphenyl)benzotriazole and 2-(3-t-butyl-5-methyl-2-hydroxyphenyl)-5-chlorobenzotriazole, but are not limited to these UV absorbing agents. The pigment and the UV absorbing agent described above are preferably added in a proportion of about 0.01 to 5 wt % to the plastic material for the light ray barrier layer.

For the formation of the layer having the gas permeation preventing capability (gas barrier property) particularly for the formation of the layer having the oxygen barrier property, an oxygen absorbing agent such as iron, sodium hydrogen sulfite, sodium sulfite, pyrogallol, ascorbic acid or tocopherol may be blended in the plastic material. The oxygen absorbing agent is preferably added in a proportion of about 0.15 to about 5 wt % to the plastic material for the oxygen barrier layer.

In general, layers other than the functional layer in the drug solution filling plastic ampoule according to the present invention are each preferably composed of a polyolefin. Examples of the polyolefin include various polyolefins such as polyethylene and polypropylene which are conventionally used as materials for medical plastic containers. As required, an adhesive resin such as a polyethylene modified with an unsaturated carboxylic acid, an ethylene-acrylic acid copolymer or an ethylene-vinyl acetate copolymer may be provided between the layers. The levels of the characteristic properties (e.g., the density, the MFR and the like) of the plastic material for the other layers may be properly selected from wide ranges according to the laminate structure and the shape of the container to be produced.

The polyolefin usable in the present invention is not particularly limited, but any of various conventionally known polyolefins may be used. It is particularly preferred to use polyethylene or polypropylene among the various polyolefins.

Any of various types of polyethylenes (PE) including low density (branched) polyethylenes (HP-LDPE) prepared by a so-called high pressure method, linear low density polyethylenes (LLDPE), medium density polyethylenes (MDPE) and high densitypolyethylenes (HDPE) may be used as the polyethylene (PE) The density of the PE may be properly selected from an ordinary PE density range of 0.900 g/cm$^3$ to 0.965 g/cm$^3$. From the viewpoint of the moldability with the polycycloolefin layer and the dynamic properties of the ampoule, it is preferred that the density of the polyethylene is selected from a relatively low density range, more specifically from a range of 0.910 to 0.930 g/cm$^3$. From the viewpoint of the moldability with the polycycloolefin layer and the dynamic properties of the ampoule, it is preferred that the PE has a melt flow rate (MFR) of 0.2 to 20 g/10 min (at 190° C.).

The PE is not limited to a homopolymer, but may be a copolymer. In this case, exemplary comonomers include α-olefins such as butene-1, pentene-1, hexene-1, 4-methylpentene-1, octene-1 and decene-1. Any of these comonomers is preferably present in the copolymer in a proportion of not greater than 20 mol %, more preferably about 3 to about 20 mol %.

The type and properties of the polypropylene (PP) are not particularly limited, but it is preferred to employ a commonly used isotactic PP or syndiotactic PP (i.e., a crystalline homopolymer) or a crystalline copolymer essentially containing these polypropylenes. Preferred examples of comonomers for the crystalline copolymer include α-olefins such as ethylene and butene-1. Any of these comonomers is preferably present in the copolymer in a proportion of not greater than 30 mol %, more preferably about 2 to about 30 mol %, further more preferably about 3 to about 25 mol %. From the viewpoint of the moldability with the polycycloolefin layer and the dynamic properties of the ampoule, it is preferred that the PP has a melt flow rate (MFR) of 0.2 to 20 g/10 min (at 190° C.).

For imparting the inventive plastic ampoule with the oxygen permeation preventing capability (oxygen barrier property), an oxygen absorbing agent such as iron, sodium hydrogen sulfite, sodium sulfite, pyrogallol, ascorbic acid or tocopherol may be blended in the plastic material. The oxygen absorbing agent is preferably added in a proportion of about 0.15 to about 5 wt % to the plastic material for the oxygen barrier layer. A stabilizer such as butylhydroxytoluene or octadecyl-3-(3,5-di-t-butyl-4-hydroxyphenyl)propionate, an antibacterial agent such as silver-zeolite or cypress thiol and/or a plasticizer such as a phthalate may be blended in a proper amount in the plastic material for the inventive plastic ampoule. Where the plastic material containing any of these additives is used, the ampoule is preferably formed from a laminate material in which a layer of the additive-containing plastic material is provided as other than the layer defining the interior surface of the ampoule.

Layer Structure of Ampoule

The innermost layer of the inventive drug solution filling plastic ampoule is preferably composed of a polyolefin typified by polyethylene and polypropylene or a polycycloolefin. As described above, the polyolefin and the polycycloolefin are highly safe and stable against a drug and a drug solution, and excellent in fusion-bondability.

In order to sufficiently ensure the function and effect of the drug barrier layer, the layer having the drug permeation preventing capability (drug barrier property) is preferably provided outward of the innermost layer of the plastic ampoule and inward of the other functional layers.

Additives to be Blended

As required, additives may be blended in the plastic material for the drug solution filling plastic ampoule according to the present invention. As required, a stabilizer such as butylhydroxytoluene or octadecyl-3-(3,5-di-t-butyl-4-hydroxyphenyl)propionate, an antibacterial agent such as silver-zeolite or cypress thiol and/or a plasticizer such as a phthalate may be blended in a proper amount in the plastic material for the inventive plastic ampoule.

The layer containing any of these additives is preferably provided outward of the drug barrier layer.

Production Method

The drug solution filling plastic ampoule according to the present invention can be produced by using a blow-fill-seal machine including a multilayer extruder and a multilayer blow die.

More specifically, a tubular parison having two or more layers is extruded through the multilayer blow die. The parison includes at least one functional layer having at least one characteristic property selected from the group consisting of the gas permeation preventing capability (gas barrier property), the steam permeation preventing capability (moisture barrier property), the light ray permeation preventing capability (light ray barrier property), the drug permeation preventing capability (drug barrier property) and the drug absorption/adsorption preventing capability. A container body is molded by holding the tubular parison between lower split mold pieces (for container body molding) and injecting air into the inside of the parison or sucking the parison from mold face holes, and a predetermined amount of a predetermined drug solution is filled in the container body. Further, a fusion-bonded portion which seals a mouth of the container body and a holder tab which is connected to the fusion-bonded portion to be used for wrenching off the fusion-bonded portion are formed by holding the mouth of the container body between upper split mold pieces. Thus, the drug solution filling plastic ampoule according to the present invention is produced. The layer structure of the parison is properly determined according to a layer structure required for the drug solution filling plastic ampoule.

Conditions for the production of the ampoule by the blow-fill-seal process are not particularly limited, but the production of the ampoule may be achieved under ordinary production conditions. A parison melt-extrusion temperature and a melt-extrusion rate are properly determined according to the resin to be used, the shape of the container to be molded, and the like.

The thickness of the drug solution filling plastic ampoule is preferably about 300 to about 2000 μm. The thickness of the functional layer is not particularly limited, but may be properly determined according to the function of the functional layer and the use purpose of the ampoule. In general, the thickness of the functional layer is preferably about 10 to about 300 μm.

Drug and Drug Solution to be Contained

A drug solution to be contained in the inventive plastic ampoule is not particularly limited, but may be selected according to the functional properties of the functional layer.

A solution of an easily oxidizable drug may be contained in the plastic ampoule including the layer having the gas permeation preventing capability (gas barrier property) according to the present invention. Examples of the easily oxidazable drug include vitamins such as vitamin A, amino acids such as cysteine and tryptophan, reduced glutathione, fat emulsion preparations and ribosome preparations.

A solution of a photo-degradable drug may be contained in the plastic ampoule including the layer having the light ray permeation preventing capability (light ray barrier property) according to the present invention. Examples of the photo-degradable drug include vitamins such as vitamin $B_2$ and vitamin $B_{12}$, bromhexine hydrochloride, saccharated iron oxide, atropine sulfate, neostigmine, aminopropylon, haloperidol and ephedrine hydrochloride.

A solution of an absorptive/adsorptive drug may be contained in the plastic ampoule including the layer having the drug absorption/adsorption preventing capability according to the present invention. Examples of the absorptive/adsorptive drug include vitamins such as vitamin D, nitroglycerin and elcatonin.

EXAMPLES

The inventive drug solution filling plastic ampoule will hereinafter be described by way of examples.

The acronyms and properties of ingredients for the drug solution filling plastic ampoule are shown below.

Polyolefins

PE1: A copolymer of ethylene and 1-butene (having a density of 0.92 g/cm$^3$ and a melt flow rate (MFR) of 1.0 g/10 min (at 190° C.) and available under the trade name of ULTZEX 2010B from Mitsui Chemicals Inc.)

PE2: A plastic material prepared by blending organic pigments (available under the trade names of CHROMOPHTHAL YELLOW GR and CHROMOPHTHAL YELLOW AGR from Ciba Geigy Corporation) in proportions of 0.2 wt % each in PE1 (a plastic material having the UV permeation preventing capability (UV barrier property))

PE3: A plastic material prepared by blending 10 wt % of sodium sulfite (having an average particle diameter of about 8 μm) as an oxygen absorbing agent in PE1 (a plastic material having the oxygen permeation preventing capability (oxygen barrier property))

PP1: An isotactic polypropylene (having a density of 0.91 g/cm$^3$ and an MFR of 1.6 g/10 min (at 230° C.) and available under the product number J704 from Mitsui Chemicals Inc.)

PP2: A plastic material prepared by blending organic pigments (available under the trade names of CHROMOPHTHAL YELLOW GR and CHROMOPHTHAL YELLOW AGR) in proportions of 0.2 wt % each in PP1 (a plastic material having the UV permeation preventing capability)

Modified Polyolefin

AD1: A maleic acid modified polyethylene (having a density of 0.92 g/cm$^3$ and an MFR of 0.9 g/10 min (at 190° C.) and available under the trade name of ADMER NB550 from Mitsui Chemicals Inc.)

Polyol

EVOH1: A copolymer of ethylene and vinyl alcohol (having a melting point of 175° C. and an MFR of 1.6 g/10 min (at 190° C.) and available under the trade name of EVAL EP-H101 from Kurare Co., Ltd.)

Polycycloolefins

COP1: A material prepared by ring-opening polymerization of a norbornene monomer and hydrogenation of the resulting polymer (having a specific gravity of 1.01, an MFR of 20 g/min (at 280° C.) and a glass transition temperature (Tg) of 105° C. and available under the trade name of ZEONOR 1020R from Nippon Zeon Co., Ltd.)

COP2: A material prepared by ring-opening polymerization of a norbornene monomer and hydrogenation of the resulting polymer (having a specific gravity of 1.01, an MFR of 27 g/min (at 280° C.) and a Tg of 70° C. and available under the trade name of ZEONOR 750R from Nippon Zeon Co., Ltd.)

COP3: A material prepared by ring-opening polymerization of a norbornene monomer and hydrogenation of the resulting polymer (having a specific gravity of 1.01, an MFR of 20 g/min (at 280° C.) and a Tg of 136° C. and available under the trade name of ZEONOR 1420R from Nippon Zeon Co., Ltd.)

COC1: A copolymer of ethylene and tetracyclododecene (having a specific gravity of 1.03, an MFR of 25 g/10 min (at 260° C.) and a Tg of 105° C. and available under the trade name of APEL APL6011T from Mitsui Chemicals Inc.)

COC2: A copolymer of ethylene and tetracyclododecene (having a specific gravity of 1.02, an MFR of 40 g/10 min (at 190° C.) and a Tg of 80° C. and available under the trade name of APEL APL6509 from Mitsui Chemicals Inc.)

COC3: A copolymer of ethylene and tetracyclododecene (having a specific gravity of 1.02, an MFR of 40 g/10 min (at 190° C.) and a Tg of 70° C. and available under the trade name of APEL APL8008 from Mitsui Chemicals Inc.)

Polyamide

NY1: A material prepared by polycondensation of m-xylylenediamine and adipic acid (having a melting point of 243° C. and available under the trade name of MX NYLON 6001 from Mitsubishi Gas Chemical Company Inc.)

Polyester

PET1: Polyethylene terephthalate (available under the trade name of MITSUI PET from Mitsui Chemicals Inc.) Production of Drug Solution Filling Plastic Ampoules

Example 1

With the use of a blow-fill-seal machine having a double layer blow die, a drug solution filling plastic ampoule of a double layer structure (having a volume of 10 mL) including an inner layer of COP1 (polycycloolefin) and an outer layer of PE1 (polyolefin) and filled with 10 mL of a 0.005% nitroglycerine aqueous solution was produced. This ampoule 10 had a shape as shown in FIG. 1. The inner layer and the outer layer of the ampoule had thicknesses of 100 μm and 700 μm, respectively, at the body of the ampoule.

Example 2

With the use of a blow-fill-seal machine having a double layer blow die, a drug solution filling plastic ampoule of a double layer structure (having a volume of 20 mL) including an inner layer of a plastic material prepared by blending COP1 (polycycloolefin) and PE1 (polyolefin) in a weight ratio of 50:50 and an outer layer of PP1 (polyolefin) and filled with 20 mL of a 0.005% nitroglycerine aqueous solution was produced. This ampoule 10 had a shape as shown in FIG. 1. The inner layer and the outer layer of the ampoule had thicknesses of 100 μm and 700 μm, respectively, at the body of the ampoule.

Example 3

With the use of a blow-fill-seal machine having a triple layer blow die, a drug solution filling plastic ampoule of a triple layer structure (having a volume of 10 mL) including an inner layer of PE1 (polyolefin), an intermediate layer of COP1 (polycycloolefin) and an outer layer of PE1 and filled with 10 mL of a 0.005% nitroglycerine aqueous solution was produced. This ampoule 10 had a shape as shown in FIG. 1. The inner layer, the intermediate layer and the outer layer of the ampoule had thicknesses of 50 µm, 100 µm and 700 µm, respectively, at the body of the ampoule.

Example 4

A drug solution filling plastic ampoule of a triple layer structure was produced in substantially the same manner as in Example 3, except that a plastic material prepared by blending COP1 (polycycloolefin) and PE1 (polyolefin) in a weight ratio of 50:50 was used as the plastic material for the intermediate layer instead of COP1 only, the volume of the ampoule was 5 mL, and the amount of the 0.005% nitroglycerine aqueous solution filled in the ampoule was 5 mL.

Example 5

With the use of a blow-fill-seal machine having a five layer blow die, a drug solution filling plastic ampoule of a five layer structure (having a volume of 20 mL) including an inner layer of PE1 (polyolefin), an inner intermediate layer of a plastic material prepared by blending COP1 (polycycloolefin) and PE1 in a weight ratio of 50:50, a middle intermediate layer of COP1, an outer intermediate layer of a plastic material prepared by blending COP1 and PE1 in a weight ratio of 50:50 and an outer layer of PE1 and filled with 20 mL of a 0.005% nitroglycerine aqueous solution was produced. This ampoule 10 had a shape as shown in FIG. 1. The inner layer, the intermediate layers (the inner, middle and outer intermediate layers) and the outer layer of the ampoule had thicknesses of 50 µm, 100 µm and 500 µm, respectively, at the body of the ampoule.

Example 6

A drug solution filling plastic ampoule of a five layer structure was produced in substantially the same manner as in Example 5, except that a plastic material prepared by blending COP1 (polycycloolefin) and PE1 (polyolefin) in a weight ratio of 80:20 was used instead of COP1 only as the plastic material for the middle intermediate layer, the volume of the ampoule was 10 mL, and the amount of the 0.005% nitroglycerine aqueous solution filled in the ampoule was 10 mL.

Evaluation of Properties of Plastic Ampoules

The drug solution filling plastic ampoules of Examples 1 to 6 were autoclaved at 106° C. for 40 minutes, and then stored at 60° C. for two weeks. Thereafter, the nitroglycerine content of the nitroglycerine aqueous solution filled in each of the ampoules was measured. It is noted that nitroglycerine is a highly absorptive and adsorptive drug.

As can be understood from the measurement results, the absorption and adsorption of nitroglycerine in/on the interior surfaces of the ampoules and the permeation and leakage of nitroglycerine out of the ampoules were sufficiently suppressed with not less than 95 wt % of nitroglycerine remaining in the respective ampoules after the two week storage. That is, the ampoules of Examples 1 to 6 were excellent in drug absorption/adsorption preventing capability and drug permeation preventing capability. This is supposedly because the ampoules of Examples 1 to 6 each included the polycycloolefin layer.

TABLE 1

|  | Inner layer | Intermediate layers | | | Outer layer | Volume (mL) |
| --- | --- | --- | --- | --- | --- | --- |
|  |  | Inner | Middle | Outer |  |  |
| Example 1 | COP1<br>100 µm | — | — | — | PE1<br>700 µm | 10 |
| Example 2 | COP1 + PE1<br>(50:50)<br>100 µm | — | — | — | PP1<br>700 µm | 20 |
| Example 3 | PE1<br>50 µm | — | COP1<br>100 µm | — | PE1<br>700 µm | 10 |
| Example 4 | PE1<br>50 µm | — | COP1 + PE1<br>(50:50)<br>100 µm | — | PE1<br>700 µm | 5 |
| Example 5 | PE1<br>50 µm | COP1 + PE1<br>(50:50)<br>100 µm | COP1<br>100 µm | COP1 + PE1<br>(50:50)<br>100 µm | PE1<br>500 µm | 20 |
| Example 6 | PE1<br>50 µm | COP1 + PE1<br>(50:50)<br>100 µm | COP1 + PE1<br>(80:20)<br>100 µm | COP1 + PE1<br>(50:50)<br>100 µm | PE1<br>500 µm | 10 |

Upper line: Material
Middle line: Mixing ratio (weight ratio) of resins
Lower line: Thickness of layer Production of Drug Solution Filling Plastic Ampoules Example 7

With the use of a blow-fill-seal machine having a triple layer blow die, a drug solution filling plastic ampoule of a triple layer structure (having a volume of 10 mL) including an inner layer of PE1 (polyolefin), an intermediate layer of EVOH1 (polyol) and an outer layer of PE1 and filled with 10 mL of a 0.1% tryptophan aqueous solution was produced. This ampoule 10 had a shape as shown in FIG. 1. The inner layer, the intermediate layer and the outer layer of the ampoule had thicknesses of 50 µm, 100 µm and 700 µm, respectively, at the body of the ampoule.

Example 8

With the use of a blow-fill-seal machine having a five layer blow die, a drug solution filling plastic ampoule of a five layer structure (having a volume of 5 mL) including an inner layer of PE1 (polyolefin), an inner intermediate layer of AD1 (modified polyolefin), a middle intermediate layer of EVOH1 (polyol), an outer intermediate layer of AD1 and an outer layer of PE1 and filled with 5 mL of a 0.1% tryptophan aqueous solution was produced. This ampoule 10 had a shape as shown in FIG. 1. The inner layer, the inner and outer intermediate layers, the middle intermediate layer and the outer layer of the ampoule had thicknesses of 50 μm, 10 μm, 100 μm and 700 μm, respectively, at the body of the ampoule.

Example 9

With the use of a blow-fill-seal machine having a four layer blow die, a drug solution filling plastic ampoule of a four layer structure (having a volume of 10 mL) including an inner layer of PE1 (polyolefin), an inner intermediate layer of PE3 (oxygen barrier plastic), an outer intermediate layer of EVOH1 (polyol) and an outer layer of PE1 and filled with 10 mL of a 0.1% tryptophan aqueous solution was produced. This ampoule 10 had a shape as shown in FIG. 1. The inner layer, the intermediate layers (the inner and outer intermediate layers) and the outer layer of the ampoule had thicknesses of 50 μm, 100 μm and 600 μm, respectively, at the body of the ampoule.

Evaluation of Properties of Plastic Ampoules

The drug solution filling plastic ampoules of Examples 7 to 9 were each autoclaved at 106° C. for 40 minutes, and then stored at 60° C. for two weeks. Thereafter, the tryptophan content of the tryptophan aqueous solution filled in each of the ampoules was measured. It is noted that tryptophan is an easily oxidizable drug.

As can be understood from the measurement results, the oxidation degradation of the tryptophan was sufficiently suppressed with not less than 95 wt % of tryptophan remaining in the respective ampoules after the two week storage. That is, the ampoules of Examples 7 to 9 were excellent in gas permeation preventing capability (gas barrier property, particularly oxygen barrier property) and drug permeation preventing capability. This is supposedly because the ampoules of Examples 7 to 9 each included the polyol layer.

Production of Drug Solution Filling Plastic Ampoule

Example 10

With the use of a blow-fill-seal machine having a triple layer blow die, a drug solution filling plastic ampoule of a triple layer structure (having a volume of 10 mL) including an inner layer of PE1 (polyolefin), an intermediate layer of COP1 (polycycloolefin) and an outer layer of PE2 (UV barrier plastic) and filled with 10 mL of a 0.05% vitamin B2 aqueous solution was produced. This ampoule 10 had a shape as shown in FIG. 1. The inner layer, the intermediate layer and the outer layer of the ampoule had thicknesses of 50 μm, 100 μm and 700 μm, respectively, at the body of the ampoule.

Evaluation of Properties of Plastic Ampoule

The drug solution filling plastic ampoule of Example 10 was autoclaved at 106° C. for 40 minutes, and then stored at 60° C. for two weeks. Thereafter, the vitamin B2 content of the vitamin B2 aqueous solution filled in the ampoule was measured. It is noted that vitamin B2 is a photo-degradable drug.

As can be understood from the measurement result, the photo-degradation of the vitamin B2 was sufficiently suppressed with not less than 95 wt % of vitamin B2 remaining in the ampoule after the two week storage. That is, the ampoule of Example 10 was excellent in light ray permeation preventing capability (light ray barrier property). This is supposedly because the ampoule of Example 10 included the layer containing the colorant (organic pigment).

It is also found that the leach-out of the pigment of the outer layer into the vitamin B2 aqueous solution was sufficiently suppressed. This is supposedly because the polycycloolefin layer was provided inward of the layer containing the colorant (organic pigment).

Production of Drug Solution Filling Plastic Ampoule

Example 11

With the use of a blow-fill-seal machine having a five layer blow die, a drug solution filling plastic ampoule of a five layer structure (having a volume of 2 mL) including an inner layer of PE1 (polyolefin), an inner intermediate layer of AD1 (modified polyolefin), a middle intermediate layer of NY1 (polyamide prepared by polycondensation of m-xylylenediamine and adipic acid), an outer intermediate layer of AD1 and an outer layer of PP2 (UV barrier plastic) and filled with 2 mL of a 400 IU/mL retinol palmitate solubilized solution was produced. This ampoule 10 had a shape as shown in FIG. 1. The inner layer, the inner and outer intermediate layers, the middle intermediate layer and the outer layer of the ampoule had thicknesses of 50 μm, 10 μm, 100 μm and 500 μm, respectively, at the body of the ampoule.

Evaluation of Properties of Plastic Ampoule

The drug solution filling plastic ampoule of Example 11 was autoclaved at 106° C. for 40 minutes, and then stored at 60° C./60% RH for two weeks. Thereafter, the retinol palmitate content of the retinol palmitate solubilized solution filled in the ampoule was measured. It is noted that retinol palmitate is an easily oxidizable and photo-degradable drug.

As can be understood from the measurement result, the oxidation degradation and photo-degradation of the retinol palmitate were sufficiently suppressed with not less than 95 wt % of retinol palmitate remaining in the ampoule after the two week storage. That is, the ampoule of Example 11 was excellent in gas permeation preventing capability (gas barrier property, particularly oxygen barrier property) and light ray permeation preventing capability (light ray barrier property). This is supposedly because the ampoule of Example 11 included the polyamide layer and the layer containing the colorant (organic pigment).

It is also found that the leach-out of the pigment of the outer layer into the retinol palmitate solubilized solution was sufficiently suppressed. This is supposedly because the polyamide layer was provided inward of the layer containing the pigment (organic pigment).

The layer structures of the plastic ampoules of Examples 7 to 11 are collectively shown in Table 2.

TABLE 2

| | Inner layer | Intermediate layers | | | Outer layer | Volume (mL) |
|---|---|---|---|---|---|---|
| | | Inner | Middle | Outer | | |
| Example 7 | PE1 50 μm | — | EVOH1 100 μm | — | PE1 700 μm | 10 |
| Example 8 | PE1 50 μm | AD1 10 μm | EVOH1 100 μm | AD1 10 μm | PE1 700 μm | 5 |
| Example 9 | PE1 50 μm | PE3 100 μm | — | EVOH1 100 μm | PE1 600 μm | 10 |
| Example 10 | PE1 50 μm | — | COP1 100 μm | — | PE2 700 μm | 10 |

TABLE 2-continued

| | Inner layer | Intermediate layers | | | Outer layer | Volume (mL) |
|---|---|---|---|---|---|---|
| | | Inner | Middle | Outer | | |
| Example 11 | PE1 50 μm | AD1 10 μm | NY1 100 μm | AD1 10 μm | PE2 500 μm | 2 |

Upper line: Material
Middle line: Mixing ratio (weight ratio) of resins
Lower line: Thickness of layer Production of Drug Solution Filling Plastic Ampoules Example 12

With the use of a blow-fill-seal machine having a double layer blow die, drug solution filling plastic ampoules of a double layer structure each including an inner layer of COP2 (polycycloolefin) and an outer layer of PE1 (polyolefin) and filled with 10 mL of physiological saline were produced. The ampoules 18 were provided in the form of a five-ampoule sequence as shown in FIG. 2. The inner and outer layers of the ampoules had thicknesses of 200 μm and 500 μm, respectively, at the bodies of the ampoules.

Example 13

With the use of a blow-fill-seal machine having a double layer blow die, drug solution filling plastic ampoules of a double layer structure each including an inner layer of COP2 (polycycloolefin) and an outer layer of COP3 (polycycloolefin) and filled with 10 mL of physiological saline were produced. The ampoules 18 were provided in the form of a five-ampoule sequence as shown in FIG. 2. The inner and outer layers of the ampoules had thicknesses of 200 μm and 500 μm, respectively, at the bodies of the ampoules.

Example 14

With the use of a blow-fill-seal machine having a double layer blow die, drug solution filling plastic ampoules of a double layer structure each including an inner layer of COC1 (polycycloolefin) and an outer layer of PE1 (polyolefin) and filled with 10 mL of physiological saline were produced. The ampoules 18 were provided in the form of a five-ampoule sequence as shown in FIG. 2. The inner and outer layers of the ampoules had thicknesses of 200 μm and 500 μm, respectively, at the bodies of the ampoules.

Example 15

With the use of a blow-fill-seal machine having a double layer blow die, drug solution filling plastic ampoules of a double layer structure each including an inner layer of COC2 (polycycloolefin) and an outer layer of PE1 (polyolefin) and filled with 10 mL of physiological saline were produced. The ampoules 18 were provided in the form of a five-ampoule sequence as shown in FIG. 2. The inner and outer layers of the ampoules had thicknesses of 200 μm and 500 μm, respectively, at the bodies of the ampoules.

Example 16

With the use of a blow-fill-seal machine having a double layer blow die, drug solution filling plastic ampoules of a double layer structure each including an inner layer of COC3 (polycycloolefin) and an outer layer of PE1 (polyolefin) and filled with 10 mL of physiological saline were produced. The ampoules 18 were provided in the form of a five-ampoule sequence as shown in FIG. 2. The inner and outer layers of the ampoules had thicknesses of 200 μm and 500 μm, respectively, at the bodies of the ampoules.

Comparative Example 1

With the use of a blow-fill-seal machine, plastic ampoules of a single layer structure composed of COP3 (polycycloolefin having a Tg of 136° C.) and each filled with 10 mL of physiological saline were produced. The ampoules 18 were provided in the form of a five-ampoule sequence as shown in FIG. 2, and had a wall thickness of 800 μm at the bodies thereof.

Reference Example 1

With the use of a blow-fill-seal machine, plastic ampoules 18 of a single layer structure composed of COP2 (polycycloolefin having a Tg of 70° C.) and each filled with 10 mL of physiological saline were produced. The ampoules 18 were provided in the form of a five-ampoule sequence as shown in FIG. 2, and had a wall thickness of 800 μm at the bodies thereof.

Reference Example 2

With the use of a blow-fill-seal machine, plastic ampoules 18 of a single layer structure composed of COC1 (polycycloolefin having a Tg of 105° C.) and each filled with 10 mL of physiological saline were produced. The ampoules 18 were provided in the form of a five-ampoule sequence as shown in FIG. 2, and had a wall thickness of 800 μm at the bodies thereof.

Evaluation of Properties of Plastic Ampoules

The plastic ampoules of Examples 12 to 16, Comparative Example 1 and Reference examples 1, 2 were visually checked for liquid leakage. As a result, 50 ampoules of 10 five-ampoule sequences of each of Examples 12 to 16 each including the polycycloolefin inner layer having a glass transition temperature (Tg) of not higher than 110° C. were all free from the liquid leakage. On the other hand, 40 ampoules (80%) out of 50 ampoules of Comparative Example 1 suffered from the liquid leakage.

The plastic ampoules of Reference Examples 1, 2 each including the single polycycloolefin layer can be put in practical use. In this case, a polycycloolefin having a glass transition temperature of not higher than 110° C. is preferably used as the polycycloolefin for the formation of the entire ampoules. The glass transition temperature of the polycycloolefin is preferably 60 to 105° C., more preferably 60 to 80° C.

The layer structures of the plastic ampoules of Examples 12 to 16, Comparative Example 1 and Reference Examples 1, 2 are collectively shown in Table 3.

TABLE 3

| | Inner layer | Outer layer | Volume(mL) |
|---|---|---|---|
| Example 12 | COP2(70° C.) 200 μm | PE1 500 μm | 10 |
| Example 13 | COP2(70° C.) 200 μm | COP3 (70° C.) 500 μm | 10 |
| Example 14 | COC1(105° C.) 200 μm | PE1 500 μm | 10 |

TABLE 3-continued

|  | Inner layer | Outer layer | Volume(mL) |
|---|---|---|---|
| Example 15 | COC2(70° C.) 200 μm | PE1 500 μm | 10 |
| Example 16 | COC3(70° C.) 200 μm | PE1 500 μm | 10 |
| Comparative Example 1 | COP3(136° C.) 800 μm | | 10 |
| Reference Example 1 | COP2(70° C.) 800 μm | | 10 |
| Reference Example 2 | COC1(105° C.) 800 μm | | 10 |

Upper line: Material (glass transition temperature, ° C.)
Lower line: Thickness of layer

INDUSTRIAL APPLICABILITY

As described above, the present invention is applicable to a plastic ampoule for aseptically and stably storing and preserving an easily oxidizable drug, a photo-degradable drug and an absorptive/adsorptive drug, and to production of such plastic ampoule.

What is claimed is:

1. A drug solution filling plastic ampoule comprising:
   a flexible container body having a mouth and containing a drug solution;
   a fusion-bonded portion which seals the mouth of the container body;
   and a holder tab connected to the fusion-bonded portion for wrenching off the fusion-bonded portion to open the mouth of the container body, wherein
   the flexible container body, the fusion-bonded portion and the holder tab are integrally molded from a tubular parison having three or more layers including an innermost layer composed of a polyolefin, an intermediate layer composed of blends of 20 to 50 wt % of polyolefin and 50 to 80 wt % of polycycloolefin to provide the container body with a steam permeation preventing capability and a drug permeation preventing capability and an outermost layer composed of a polyolefin, and
   a thickness of the intermediate layer is from 11.8 to 35.3% of a total thickness of the three or more layers.

2. A drug solution filling plastic ampoule as set forth in claim 1, wherein
   the container body includes at least one layer other than the innermost layer and the intermediate layer that is composed of a material containing at least one additive selected from the group consisting of a colorant, a UV absorbing agent and an oxygen absorbing agent, said intermediate layer being provided inward of the additive-containing layer.

3. A drug solution filling plastic ampoule as set forth in claim 1, which is an ampoule sequence including a plurality of ampoules connected to one another via severable thin wall portions.

4. A drug solution filling plastic ampoule as set forth in claim 1, wherein
   the container body of the plastic ampoule has a volume of 0.5 to 20 mL.

5. A production method for a drug solution filling plastic ampoule comprising the steps of:
   molding a container body having a mouth by holding a tubular parison between lower split mold pieces and forming a void in the parison, the parison having three or more layers including an innermost layer composed of a polyolefin, an intermediate layer composed of blends of 20 to 50 wt % of polyolefin and 50 to 80 wt % of polycycloolefin to provide the container body with a steam permeation preventing capability and a drug permeation preventing capability and an outermost layer composed of a polyolefin,
   a thickness of the intermediate layer being from 11.8 to 35.3% of a total thickness of the three or more layers;
   filling a drug solution in the container body; and
   holding the mouth of the container body between upper split mold pieces to form a fusion-bonded portion which seals the mouth of the container body and a holder tab which is connected to the fusion-bonded portion to be used for wrenching off the fusion-bonded portion to open the mouth of the container body.

6. A drug solution filling plastic ampoule production method as set forth in claim 5, wherein
   the parison includes at least one layer other than the innermost layer and the intermediate layer that is composed of a material containing at least one additive selected from the group consisting of a colorant, a UV absorbing agent and an oxygen absorbing agent, said intermediate layer being provided inward of the additive-containing layer.

* * * * *